US010713856B2

(12) United States Patent
Lee et al.

(10) Patent No.: US 10,713,856 B2
(45) Date of Patent: Jul. 14, 2020

(54) MEDICAL IMAGING SYSTEM BASED ON HMDS

(71) Applicants: Stewart Ping Lee, Shenzhen (CN); David Wei Lee, Shenzhen (CN)

(72) Inventors: Stewart Ping Lee, Shenzhen (CN); David Wei Lee, Shenzhen (CN)

(*) Notice: Subject to any disclaimer, the term of this patent is extended or adjusted under 35 U.S.C. 154(b) by 0 days.

(21) Appl. No.: 16/421,750

(22) Filed: May 24, 2019

(65) Prior Publication Data

US 2019/0279416 A1 Sep. 12, 2019

Related U.S. Application Data

(63) Continuation of application No. PCT/CN2017/112495, filed on Nov. 23, 2017.

(51) Int. Cl.
*G06T 19/20* (2011.01)
*G06F 19/00* (2018.01)
*G06T 15/00* (2011.01)

(52) U.S. Cl.
CPC ............ *G06T 19/20* (2013.01); *G06F 19/321* (2013.01); *G06T 15/005* (2013.01); *G06T 2210/41* (2013.01); *G06T 2219/2016* (2013.01)

(58) Field of Classification Search
CPC ..... G06T 15/08; G06T 15/005; G06T 19/003; G06T 19/20; G06T 2210/41; G06T 2219/2016; G16H 30/40; G06F 16/53; G06F 16/51; G06F 3/04815; G06F 19/321; G06F 3/04842
See application file for complete search history.

(56) References Cited

U.S. PATENT DOCUMENTS

| | | | | |
|---|---|---|---|---|
| 8,976,190 | B1* | 3/2015 | Westerhoff | A61B 6/465 345/581 |
| 2004/0259065 | A1* | 12/2004 | Geiger | G06T 5/40 434/272 |
| 2007/0008317 | A1* | 1/2007 | Lundstrom | G06T 15/08 345/424 |
| 2016/0171157 | A1* | 6/2016 | Mielekamp | A61B 5/742 345/589 |

OTHER PUBLICATIONS

Gutenko, Ievgeniia, et al. "Remote volume rendering pipeline for mHealth applications." Medical Imaging 2014: PACS and Imaging Informatics: Next Generation and Innovations. vol. 9039. International Society for Optics and Photonics, 2014. (Year: 2014).*

* cited by examiner

*Primary Examiner* — Daniel F Hajnik
(74) *Attorney, Agent, or Firm* — Imperium Patent Works; Zheng Jin

(57) ABSTRACT

Disclosed in the present invention are a medical imaging system and method based on virtual reality technique and capable of carrying out interactive and three-dimensional dynamic real-time rendering. The medical imaging system, including a local medical imaging device, a server and a terminal medical imaging device, can realize dynamic real time rendering, and realize more real, steric and intuitive the imaging effect. Based on the system and method, the doctor can realize positioning zoom, rotation, "entering", moving up and down, change in color and transparency in a particular area and the like of three-dimensional imaging to realize the interactive display of three-dimensional image.

12 Claims, 12 Drawing Sheets

MEDICAL IMAGING SYSTEM BASED ON HMDS

CROSS REFERENCE TO RELATED APPLICATIONS

This application is filed under 35 U.S.C. § 111(a) and is based on and hereby claims priority under 35 U.S.C. § 120 and § 365(c) from International Application No. PCT/CN2017/112495, with an international filing date of Nov. 23, 2017, which in turn claims priority from CN Application Number 201611055308.1 filed on Nov. 25, 2016. This application is a continuation of International Application No. PCT/CN2017/112495, which claims priority from CN Application No. 201611055308.1. International Application No. PCT/CN2017/112495 is pending as of the filing date of this application, and the United States is a designated state in International Application No. PCT/CN2017/112495. This application claims priority under 35 U.S.C. § 120 and § 365(c) from CN Application Number 201611055308.1 filed on Nov. 25, 2016. The disclosure of each of the foregoing documents is incorporated herein by reference.

TECHNICAL FIELD

The invention belongs to the field of medical devices, and specifically relates to the technical field of combination of medical image processing and computational visualization, in particular to a medical imaging system and method based on Virtual reality interaction, three-dimensional and dynamic real time rendering, HMDS.

BACKGROUND

In the prior art, doctors mostly use continuous two-dimensional slicing data to obtain the morphology, location, topological structure and other information of pathological tissue by CT (Computed Tomography), MRI (Magnetic Resonance Imaging), DTI (Diffusion Tensor Imaging), PET (Positron Emission Tomography) and other technologies.

For the existing three-dimensional editors or workstation systems, the original DICOM files will be cut, classified and destroyed, and the surface rendering effect will be finally displayed by means of surface rendering technology, as shown in FIG. 1, and the interior is black invalid data. With the existing three-dimensional imaging technology, we can only view external lesion, which means it cannot identify internal lesions and cannot distinguish the fusion of external lesion and organ. In addition, the fuzzy edge of lesion the unclear boundary, low differentiation, low number of the image frames, which cause dizziness easily, and intuitive and real internal structure of organ cannot be obtained, and the technology is mostly used to provide teaching demonstration, and it cannot effectively help doctors in diagnosis practice. In other words, the above-mentioned three-dimensional editor or workstation can only present a three-dimensional effect, and cannot do the real-time three-dimensional rendering deep into the internal organs, which is to obtain clear lesions and their edge images.

In addition, the point of how to establish the connection between local users (such as editors and developers of medical imaging system) and end users (such as doctors and patients) is becoming more and more important in the field of medical imaging technology, so that the terminal users can realize the dynamic real time rendering of three-dimensional human body images.

In view of this, designing a new medical imaging system and method based on interactive, three-dimensional and dynamic real time rendering of virtual reality is an urgent problem to be solved by relevant technical personnel in the industry. So that it can eliminate the defects and deficiencies mentioned above of the existing technology.

SUMMARY

In order to overcome the technical problems of medical imaging system of existing technology, this invention provides an image processing system and method, with which the three-dimensional human body imaging effect is more real, spatial and intuitive. The doctor can do positioning zoom, rotation, moving from top to bottom and around angles after entering into organs or lesions, and changing colors and transparency in a particular area, so as to realize the interactive display of three-dimensional imaging.

For realizing the above invention, in the first part of this invention, an image processing system is disclosed, including: 1) A local medical imaging device, comprising a local database and a reverse rendering editor, wherein the local database comprises a parsing module and a storage module. The parsing module is used to parse the first DICOM file to form the first volume texture data and save in the storage module. The reverse rendering editor is used for receiving the first volume texture data and generating the corresponding transfer function result through the transfer function model; 2) A server connected with the local medical imaging device for storing the first volume texture data and the corresponding transfer function results; 3) A terminal medical imaging device, including a user input interface and a volume database, wherein the volume database is connected with the server and used to obtaining the first volume texture data and the corresponding transfer function results. And the volume database is used to parse the second DICOM file input from the user input interface to form the second volume texture data, then the volume database find the first volume texture data and the transfer function results with the matching degree within a preset threshold, and show the first three-dimensional image; 4) When the matching degree is higher than the preset threshold, the terminal medical imaging device will transfer the second volume texture data to the local medical imaging device through the volume database, and the reverse rendering editor edit and adjust the transfer function model and transfer function results. Then the reverse rendering editor transmit the adjusted transfer function results to the terminal medical imaging device through the server and show the second three-dimensional image; and 5) One or more displays configured on the local medical imaging device and/or the terminal medical imaging device respectively.

In another preferred case, the first DICOM file is the same as the second DICOM file. In another preferred example, both the local medical imaging device and the terminal imaging medical device are equipped with a head-mounted display. In another preferred example, the head-mounted display is a VR device.

In the second aspect of the invention, the invention discloses an image processing method performed by the image processing system provided in the first aspect of the invention, including the steps as follows: (i) Obtaining the first volume texture data and the corresponding transfer function results from the server, and saving them in the volume database; (ii) Providing a second DICOM file to the terminal medical imaging device; (iii) Searching the first texture data and the corresponding transfer function results within a preset threshold matching to the second DICOM file in the volume database, and displaying the second three-dimensional image.

In another preferred example, the step (iii) also includes a step of parsing the second DICOM file to form the second volume texture data in the volume database. In another preferred example, the second three-dimensional image is displayed via a head-mounted display, preferably including a VR device. In another preferred example, the second three-dimensional image is the same as the first three-dimensional image. In another preferred example, the matching items in step (iii) is selected from the following groups: organ parameters, frame, row, column, resolution, and/or slice thickness. In another preferred example, the second volume texture data will be transferred to the local medical imaging device through the server when the matching degree is higher than the preset threshold specified in step (iii), and then the reverse rendering editor will edit and adjust the transfer function and transfer the adjusted transfer function results to the terminal medical imaging device through the server to display the second three-dimensional image.

In the third aspect, the invention discloses an image processing method performed by the image processing system provided in the first aspect of the invention, including the steps as follows: (1) Obtaining the first texture data and the corresponding transfer function results from the server, and saving them in the database; (2) Providing a second DICOM file to the terminal medical imaging device; (3) Searching the first texture data and the corresponding transfer function results within a preset threshold matching to the second DICOM file in the volume database, and displaying the second three-dimensional image; (4) Providing a region selection command to form a selection region in the second three-dimensional image, then searching the transfer function results with a preset threshold matching degree with the selection region in the volume database, and displaying the third three-dimensional image of the selection region.

In another preferred example, the data of the selection region will be transferred to the local medical imaging device through the server when the matching degree is higher than the preset threshold specified in step (4), and then the reverse rendering editor will edit and adjust the transfer function and transfer the adjusted transfer function results to the terminal medical imaging device through the server to display the third three-dimensional image.

Compared with prior art, the technical scheme provided by this invention has the following advantages. First, for the image processing system disclosed in the invention, the volume texture data and the transfer function results in the local medical imaging device can be transferred to database to store in real time. The user only needs to directly insert the original image data of the patient (such as a CT disk), Then image processing system can accurately and automatically match the server according to the information similarity of the CT disk information, automatically call the transfer function result, and directly display the clear 3D volume data rendering. The effect is that the pre-diagnosis is performed directly, and the user does not need to perform any editing on all the image materials separately.

Second, in the reverse rendering editor of the image processing system provided by the invention, the high-dimensional transfer function design is adopted, by which the organ edge is clear and reasonable after three-dimensional imaging; in addition, the lesion boundary is clearly distinguished, so that the user can recognize the organ and the disease image easily.

Third, upon completion of the first three-dimensional image, the user can select a particular part or area of the first three-dimensional image for the reconstruction of the second three-dimensional image, so as to improve the design of the transfer function, eliminate interference factors, amplify the small parts (such as the lining of blood vessels or narrow internal organs, etc.) or lesion area clearly and nondestructively. At the same time, the user can modify the color and transparency value parameters. It is convenient for the user to diagnose with the clear boundary between the organ and the lesion.

Fourth, the image processing system of the invention supports the existence of multiple selection areas at the same time, and the data is controlled independently without interference, wherein the multiple selection areas represent different organ parts in CT, MRI, DTI and PET-CT data. At the same time, color transparency increases the sensory function of human eyes and enhances the display of the boundary between organs and lesions.

Fifth, the imaging effect of human body is more real, steric and intuitive, and doctors can identify the patient's organs and identify the lesions automatically.

Sixth, the image processing system realize the interactive display of three-dimensional imaging. Doctors can position, scale and rotate the view of three-dimensional imaging to achieve multi-angle viewing, and stretch the views to "enter" the body to observe, change the color and/or transparency of a specific area to highlight a specific organ or tissue structure. Under the interaction mode, users can continuously explore the interested structure in the volume data, and the system can assist the user to complete the analysis of volume data in a more flexible and convenient way.

Seventh, HMDS (Head-mounted Displays Set) enables medical imaging and three-dimensional space to be clearer, by which the dead corners can be seen that cannot be seen in two-dimensional image, and the interaction and immersion are enhanced. Eighth, servers and local databases store the data together and they can store, share and manage data and optimize resource allocation. Ninth, to ensure the security independence of each user data, special number for the special person rule is made.

Other embodiments and advantages are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

FIG. 20(*b*) is a rendering A of the second three-dimensional reconstruction of the image processing system provided by the invention to tricuspid valve lesion.

FIG. 20(*c*) is a rendering B of the second three-dimensional reconstruction of the image processing system provided by the invention to tricuspid valve lesion.

FIG. 21(*b*) a rendering A of the second three-dimensional reconstruction of the image processing system provided by the invention to aortic aneurysm.

FIG. 21(*c*) a rendering B of the second three-dimensional reconstruction of the image processing system provided by the invention to aortic aneurysm.

FIG. 22(*b*) a rendering B of the second three-dimensional reconstruction of the image processing system provided by the invention to e renal tumor.

FIG. 23(*b*) is an enlarged three-dimensional image of the image processing system provided by the invention to the inner wall of bronchus.

FIG. 25(*b*) is a three-dimensional image B of the image processing system provided by the invention to main vascular lesion.

FIG. 25(*c*) is a three-dimensional image C of the image processing system provided by the invention to main vascular lesion.

DETAILED DESCRIPTION

Figure 1:
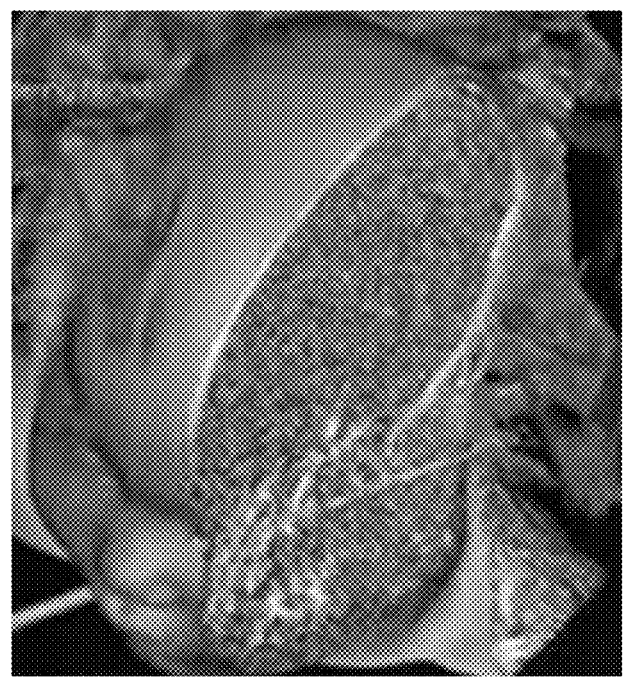
FIG. 1 is a three-dimensional human body imaging rendering based on indirect rendering of the existing technology.

Reference will now be made in detail to some embodiments of the invention, examples of which are illustrated in the accompanying drawings.

The specific embodiments of the invention are described in detail below in combination with the figures. However, the invention shall be understood to be not limited to such an implementation as described below, and the technical concept of the invention can be implemented in combination with other publicly known technologies or other technologies that have the same function.

In the description of the following concrete embodiment, many directional words will be used to describe to clearly demonstrate the structure and working mode of the invention, but the terms such as "front" and "back", "left", "right", "outside", "inside", "up", "down", "outward", "inward", "axial", "radial" and the like should be understood as easy language rather than as qualifiers.

The elements, parts or steps described in the singular and preceded by the words "one," "one piece," and "first" in this specification shall be understood that a plurality of such elements or steps are not excluded unless such exclusion is explicitly stated.

A reference to "one embodiment" of the invention is not intended to exclude the existence of additional embodiments that also contain the characteristics.

In the invention, the development side, developer and editor have the same meaning and can be used interchangeably, and they refer to an object that can operate a local medical imaging device.

In the invention, the client, user and terminal have the same meaning and can be used interchangeably. They all refer to an object that can operate terminal medical imaging devices, such as patients and doctors.

Explanation of Term

Virtual reality (VR): it refers to the simulation system that can create and experience the virtual world. It is a kind of system simulation with multi-source information fusion and interactive three-dimensional dynamic vision and entity behavior, so that users can immerse themselves in the environment.

HMDS: it refers to a head-mounted displays set for virtual reality (VR), including one or more additions, including but not limited to headset, microphone, HD camera, infrared camera, handheld tracker, position tracker, VR glasses, VR head-mounted display, VR all-in-one, VR splitter, etc.

Damage to the original DICOM file: it refers to the artificial algorithm to remove or cut and separate the original image file data to achieve the display effect of a certain organ;

Map source: it refers to the volume texture data generated by parsing the original DICOM file.

Medical imaging device: it refers to a variety of instruments that use various media as information carriers to reproduce the internal structure of the human body into image. The image information has a one-to-one correspondence with the actual structure of the human body in space and time distribution.

Local medical imaging device: it refers to a module that can be used to parse DICOM files and has the function of reverse rendering and editing. In particular, the local medical imaging device is usually located at the developer side, so as to continuously supplement, adjust, and modify the parameters, volume texture data, and corresponding transfer functions, thus the end user can avoid the trouble of self-editing and debugging. That is, based on the medical image algorithm, three-dimensional volume rendering is performed to realize the three-dimensional effect of the human body. Preferably, the local medical imaging device of the present invention supports 512*512 pixels, a total of 1024 images for read editing, or 1024*1024 pixels, for a total of 2048 images for read editing.

Terminal medical imaging device (Display System): It means that the volume texture data and the corresponding transfer function result can be updated from the server in real time, so that the end user can realize the plug-and-play imaging experience. In addition, if the transfer function result of the matching degree within a preset threshold cannot be retrieved in the database, the terminal medical imaging device can upload the DICOM file to the local medical imaging device through the server. Then the terminal medical imaging device supplement or modify the transfer function, and store the newly formed volume texture data and the corresponding transfer function result into the server to implement data update and sharing. The terminal medical imaging device described in the present invention (usually the terminal user uses the terminal medical imaging device, such as a doctor) is different from the local medical imaging device. The difference lies in the terminal medical imaging device does not include a reverse rendering editor, and the transfer function cannot be designed and edited, and the data required for 3D rendering can only be obtained from the local medical imaging device by accessing the server, such as the transfer function result of the 3D human body image.

Volume rendering: That is volume visualization rendering. Volume visualization rendering mainly includes two methods: Surface Rendering and Direct Volume Rendering. Surface rendering mainly obtains the image with stereo effect by extracting the surface information of the object and then rendering it by illumination calculation. It only uses part of the information in the volume data to form the final rendering result. It cannot get all the information of the whole volume data, and many details are lost, which is not conducive to the detailed volume data analysis of the structure, and its visualization effect is not so good. Direct Volume Rendering obtains the final rendering result by accumulating the optical properties of the voxels in the whole volume data. The rendering result is more complete, specific, and the visual effect is better. The volume visualization rendering method adopted by the invention is a direct volume rendering method which is real-time dynamic volume rendering, and the volume rendering algorithm adopts a light transmission method, which can better reflect the overall structure information in the volume data. Direct volume rendering directly categorizes the original DICOM file and assigns optical properties. It not only visualizes the important anatomical information existing only in the brain of the radiologist in three-dimensional form, but also spatially identifies the positional relationship and specific shape information of the target organ or lesion with the surrounding tissue.

Volume data: The volume data in direct volume rendering is obtained by a series of medical image data according to certain criteria. For example, if the heart data is collected at 0.33 mm scale, a heart image is obtained every 0.33 mm by cross or slitting. A set of two-dimensional cardiac images are obtained, which not only include surface detail features of the original part, but also internal structural features.

Voxel: The voxel is the pixel in the above two-dimensional image, which is the smallest unit of the volume data in the three-dimensional volume data. For example, there are m, n, and t voxel points along the x-axis, y-axis, and z-axis, respectively. The size of a volume data is m×n×t DICOM (Digital Imaging and Communications in Medicine): it refers to the standard of medical digital image and communication, which covers the acquisition, archiving, communication, display and query of medical digital images and almost all the information exchange protocols, and it defines a set of objects containing various types of medical diagnostic images and related analysis, reports and other information. DICOM file mainly consists of three parts: file header, data set and data element. Data set includes not only medical image, but also patient name, image size and other information, and data element includes identification, value representation, value length and value field, as shown in Table 1 below.

TABLE 1

| Group | Element | Identification | Value representation | Value length | Value field |
| --- | --- | --- | --- | --- | --- |
| 0018 | 0015 | Body part examined | CS | 12 | Cardiac angiography |
| 0018 | 0022 | Scan options | CS | 10 | Volume scan |
| 0018 | 0050 | Slice thickness | DS | 4 | 0.5 |
| 0018 | 0060 | KVP | DS | 4 | 120 |

As used in the invention, the first DICOM file is preferably a pre-collected medical image file by the developer, that is, the original file used to initially form the server; the second DICOM file is preferably the client, that is, the medical image file that the doctor or patient needs to diagnose. The first DICOM file and the second DICOM file can be the same or different.

Parse DICOM file: DICOM file contains four levels of attributes, namely, patient, study, series and image. Each DICOM file is parsed to get a corresponding series number and study ID value. The series number and study ID values obtained by parsing the first image will be a group, and the subsequent parsed one shall be compared with the series number and study ID values of the group identification that have been parsed before. If the Series Number and the Study ID values are the same as the previously parsed Series Number and Study ID values, they belong to the same group of data. If they are different, they are new DICOM arrays to classify the DICOM files.

Body texture data (Texture 2D/3D data): It is the volume data format formed by the DICOM file after parsing. It describes the spatial surface data and spatial 3D data in the volume data, which can be directly edited by the reverse rendering editor.

Transfer Function model: It is used interchangeably with transfer function and transfer function design. It is a function that maps the data information of a voxel to an optical attribute: $T:V_1 \times V_2 \times \ldots V_n \rightarrow O_1 \times O_2 \times \ldots O_n$, where T is the mapping rules between $V_n$ and $O_n$, domain $V_n$ represents the different attribute values of the voxel, such as the distance gradient amplitude, curvature, scale, and the gray value of CT or MRI, domain $O_n$ represents the optical characteristics and represents the different optical properties of opacity and color value. The opacity determines which structures of interest are displayed. The color values determine how the structure of interest is displayed more intuitively. The structure is typically opacity, color, shading parameters, refractive index, reflectivity, and so on. In the field of medical imaging drawing, there is currently no universal transfer function model applicable to all data. Therefore, the various transfer function models used in the this invention are adapted to different organs and/or different lesions of patients, including but not limited to: arteries, blood vessels, bones, chest, digestive tract, brain, kidney, heart, lungs, liver, stomach, pelvis, whole body, and renal tumor lesions, tricuspid heart disease lesions, aortic tumor lesions, Lung and bronchial wall, MRI brain tumor, main vascular lesions, etc.

As used by the invention, the transfer function model includes, but is not limited to, a grayscale image multidimensional transfer function, a color image multidimensional transfer function and so on. In the multidimensional transfer function of the gray image, the gradient information or the like can be calculated according to the gray scale scalar value, and the edge feature and the contour information of the volume data can be expressed, and the color value and the opacity value can be output. The color image transfer function is a self color vector and a derived attribute value calculated by the vector.

Reverse rendering editor (Editor System): it refers to the module used to receive the volume texture data and generate the transfer function result through the transfer function model. It can realize the design, modification, supplement and addition of the transfer function. Additionally, a display can be configured in the local medical imaging device for dynamically displaying the three-dimensional image effects performed by the reverse rendering editor in real time. And it can adjust the transfer function according to the three-dimensional image effect to present the best imaging effect.

Transfer function result: In the first aspect, the body texture data is edited by using different transfer function models. According to the requirements of visualizing the three-dimensional image, the mapping relationship between the appropriate volume texture data attributes and optical features is obtained, such as the cube edit box required for the transfer function, the number of arrays edited with the arc, coordinates, color, transparency, etc. In the second aspect, it is able to distinguish spatial information of voxels with different coordinates. In the third aspect, it is able to distinguish the gradient modulus of the material boundary, the curvature of the shape of the object, and so on. The transfer function results include the transfer function results of the tissue structure on the surface and inside of the patient's organs, and the transfer function results of the cubic space.

Local database: in the local medical imaging device, the local database is used to parse the first DICOM file to form the first volume texture data, classify and save the volume texture data according to the different patient, image collector, image collection time, film type and organ, and generate the unique identification. Besides, it refers to a local medical imaging device for parsing a first DICOM file to form first volume texture data. It can classify and save the body texture data according to the patient, image collector, image acquisition time, film type, and organ, and generate a unique identifier. In addition, the local database can also save the transfer function results edited in the reverse rendering editor. At the same time, the local database allows the save operation of the development side to occur at any time. It uses one of the identification criteria for saving the image with the local system time accurate to the millisecond, and supports the return to the 3D mode after the save operation is completed. The editor can continue to edit the original effect, so that the editor can continue to debug the details under the basic editing of a better image effect. This saves editing time and also supports viewing and finding data about previously edited 3D human images.

Volume database: the volume database can obtain updated transfer function results and volume texture data from the server in real time. In addition, the volume database can be used to parse the medical imaging data input by the user input interface and find the transfer function result that matches the medical image data within a predetermined threshold.

Server: it is used to store the volume texture data generated by parsing the DICOM file and the transfer function results edited in the reverse rendering editor. The DICOM file can be the medical image file collected in advance by the developer when developing the medical imaging system of the invention, i.e. the original file initially formed by the server. Alternatively, when the matching degree is less than a predetermined threshold, the user end, that is, the doctor or the patient uploads the medical image file that needs to be diagnosed, and the file is parsed by the local medical imaging device to form new volume texture data and transfer function results, and then stored in the server. Preferably, the "server" described in this invention can be a preset data set and a sum of data sets dynamically supplemented according to user requirements.

Matching: it refers to the process of matching the volume texture data formed by parsing the second DICOM file input in terminal medical imaging device with the volume texture data and transfer function results stored in the volume database in the Organ Parameters, Frame, Row, Column, Resolution Slice Thickness and other aspects. It is to find the result of the transfer function with the matching degree within a preset threshold to form a three-dimensional image. Preferably, the preset threshold defines the range of the matching degree to define the range of the matching degree. If the threshold value exceeds the preset threshold value, it will be deemed as a mismatch, and then the technicians in this field can adjust the threshold value according to the matching demand.

Preferably, the matching in the invention shall be carried out in the order of organ data, frame, row, column, resolution and slice thickness. In the invention, the matching includes but not limited to: a. Data type matching of CT disk, such as CT, DTI, MRI, PET; b. Organ data matching, resolution matching, slice thickness matching and number of three-dimensional image resources in CT disk; c. Transfer function results matching.

Embodiment 1: The Transfer Function Fitting of Color Value and Opacity Value

Figure 26:
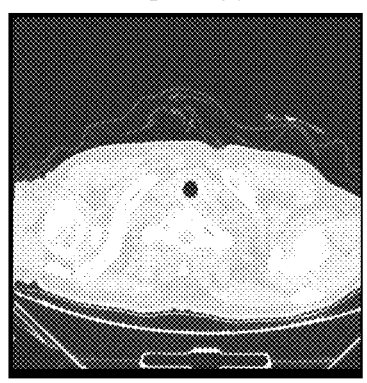
FIG. 26 is a grayscale image edited by the image processing system of the invention to reverse rendering of pulmonary CT.
Figure 27:
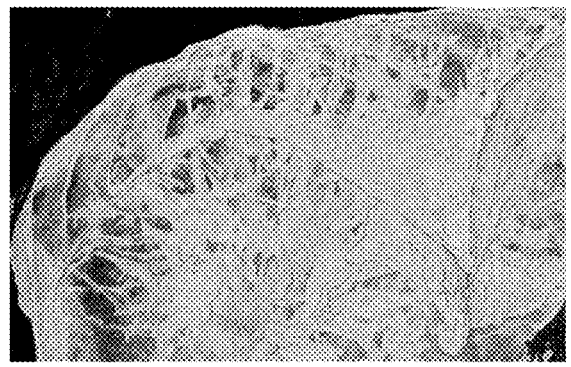
FIG. 27 is a transparency rendering of the image processing system provided by the invention to reverse rendering and editing of pulmonary CT.

At present, most of the volume data collected by most medical scanning devices are grayscale data, and different human tissues and organs have different grayscale distribution. The transfer function in the invention assigns color value and opacity value according to the different grayscale distribution in the grayscale image. As shown in FIG. 26 and FIG. 27, FIG. 26 is a grayscale image edited by reverse rendering and editing of pulmonary CT by the image processing system. FIG. 27 is the transparency rendering of the reverse rendering and editing of pulmonary CT by the image processing system. Taking a lung CT with a layer thickness of 1 mm and a frame number of 296 as an example, the specific steps are as follows:

Selection of organ area, editing of selected area properties, and getting the final transfer function for rendering.

1. Selection of Organ Area:

Function of cubic graph operation: parameters include the selected area box and the x and y coordinates entered by the mouse.

bool Cxxx_handleMoveEvent (Cxxx *p, int x, int y);

Function of curve fitting operation: parameters include the selected area box and the x and y coordinates entered by the mouse.

bool Cxxx_handleMoveEvent (Cxxx *p, int x, int y);

2. Editing of Selected Area Properties, Such as Organ Color and Transparency Adjustment (1) Color selection of selected organs realized by the transfer in three-dimensional mode Parameters are mouse x and y, and the color of the mouse position is changed within the range of color selection Implementation function: bool CTransferFunction2_move_Cxxxx (int x, int y);

(2) Adjustment of transparency of selected organ in three-dimensional mode of the editor, the transparency value is 0~1.0

The parameter is the current location representing the transparent table UI

Implementation function: void CTransferFunction2_Axxxx (int index).

Embodiment 2

In the embodiment, a two-dimensional grayscale-gradient transfer function space is used to illustrate the process of volume rendering based on a high-dimensional transfer function of this invention. The image-centric transfer function method, which is different from a data-centric transfer function method, can regard the process of obtaining the finally satisfied rendering effect as a parameter optimization process which takes transfer function as a parameter. Namely, the transfer function can be changed indirectly by taking a specific rendering result as the target. Therefore, users shall implement interactive visualization results continuously without the direct design of transfer function.

2-1 Construction of the Two-Dimensional Grayscale-Gradient Transfer Function Space:

In volume data, voxels in the same substance have similar gray value, while the gray value of voxels in the boundary region between different substances changes obviously. In the scalar field, the gradient is a measure of the direction and rate of change of the scalar field, so the gradient will change dramatically. (1) Read the volume data and calculate the gradient amplitude for each voxel; (2) Count the number of points with the same grayscale and gradient point pairs in volume data, so as to form a two-dimensional image of 255*256.

2-2 Sobel Operator:

Being different from the central difference method, Sobel operator makes use of 26 voxels in its 26 neighborhoods to obtain better display effect. The three-dimensional Sobel operator is obtained by using the convolution kernel of 3*3*3, wherein the first matrix is the previous slice, the second matrix is the current slice, and the third matrix is the next slice.

2-3 Construction of a Two-Dimensional Grayscale-Gradient Cubic Editing Box:

(1) Firstly, set the range of two-dimensional gray gradient cubic editing box as [0,255] (the initial setting is zero). Namely, assign the brightness value of each pixel in a two-dimensional image with a size of 255*256, wherein the horizontal ordinate represents the grayscale and the vertical coordinate represents the gradient.

(2) Traverse the whole volume data for the first time, then calculate the gradient amplitude $\|\nabla f\|$ of each voxel according to the formula; in the formula, h=1; the maximum value and minimum value of $\|\nabla f\|$ are counted, so as to adjust the range of gradient amplitude in the next step.

(3) Traverse the whole volume data for the second time, and map the gradient amplitude $\|\nabla f\|$ of each voxel to the range of [0,255] to ensure that the two-dimensional transfer function space can display the gradient amplitude fully, and count the number of the voxels belonging to each point pairs I $\|\nabla f\|$ in the whole volume data. Then, implement logarithmic transformation of the data value of counted point pairs to express the information of the transfer function space efficiently, wherein the brightness value is corresponding to the distribution of gray gradient point pairs of voxels in the three-dimensional volume data; specifically, the brightness is proportional to the number of the corresponding voxels.

Therefore, the number of voxels with point pairs counted for any pixel in the transfer function space is N(i,j), and the final brightness value after logarithmic transformation is I(i,j), as shown in the formula (1-1):

$$I(i, j) = \frac{\log(N(i, j))}{N_{max}} \qquad (1\text{-}1)$$

where $N_{max}$ is the maximum value of all Ns in the transfer function space after logarithmic transformation.

Embodiment 3: Workflow of an Image Processing System

Figure 2:
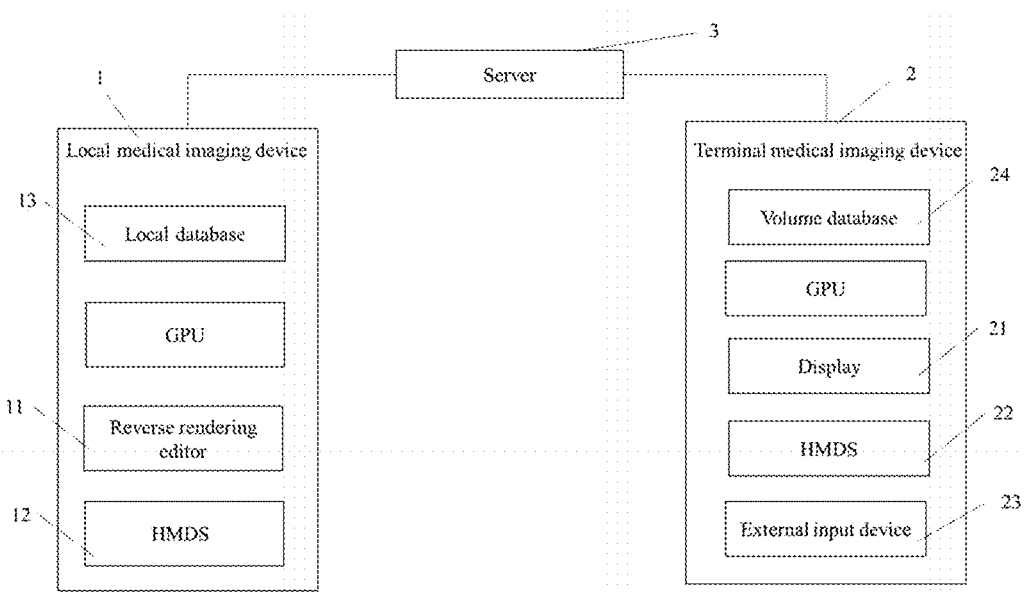
FIG. 2 is a structural diagram of the image processing system provided by the invention.

As shown in FIG. 2, it is the structural diagram of the image processing system of the invention, which mainly includes: a local medical imaging device 1, a server 3, a terminal medical imaging device 2, wherein:

The source of the volume data for medical imaging includes but not limited to CT (Computerized Tomography), MRI (Magnetic Resonance Imaging), DTI (Diffusion Tensor Imaging), PET-CT (Positron Emission Computed Tomography) and the like. It is saved by DICOM file, and each DICOM file includes file header information and data information, wherein the file header will save the data size, generation time of the file, relevant information of the patient, the position of slicing data and the like.

The local medical imaging device 1 is equipped with a CD-ROM drive to read the original DICOM files of CT, MRI, DTI and PET-CT stored in the CD-ROM provided by the developer, and the original DICOM files are parsed by the local database to generate volume texture data.

It shall be indicated that the more data source of the image group is used for volume data rendering, the better. And there are more details as the quantity of figure source data of CD data and the image data group for rendering will affect the final rendering effect. Therefore, the local medical imaging device 1 will automatically pick the figure source with the largest data to parse for the following volume rendering; furthermore, the local medical imaging device 1 will select the figure source with thin slice thickness preferentially, and the scope of slice thickness is 0.2-0.7 mm. As the amount of computation involved in the calculation process of volume rendering is large, the local medical imaging device 1 of the invention has a GPU, which can realize direct volume rendering and real-time GPU rendering by utilizing the high-speed parallel computing function.

The local medical imaging device 1 further edits and implements real-time dynamic volume rendering of volume texture data on the basis of 64-bit storage space through the reverse rendering editor 11, and designs the transfer function to obtain the mapping relationship between the appropriate volume texture data attributes and optical features and also to obtain the transfer function results. In addition, the editors can adjust and edit the transfer function reversely by watching the real-time volume rendering, and finally form a three-dimensional image with clear and reasonable organ and lesion edges and high recognition of internal structure.

Figure 3:
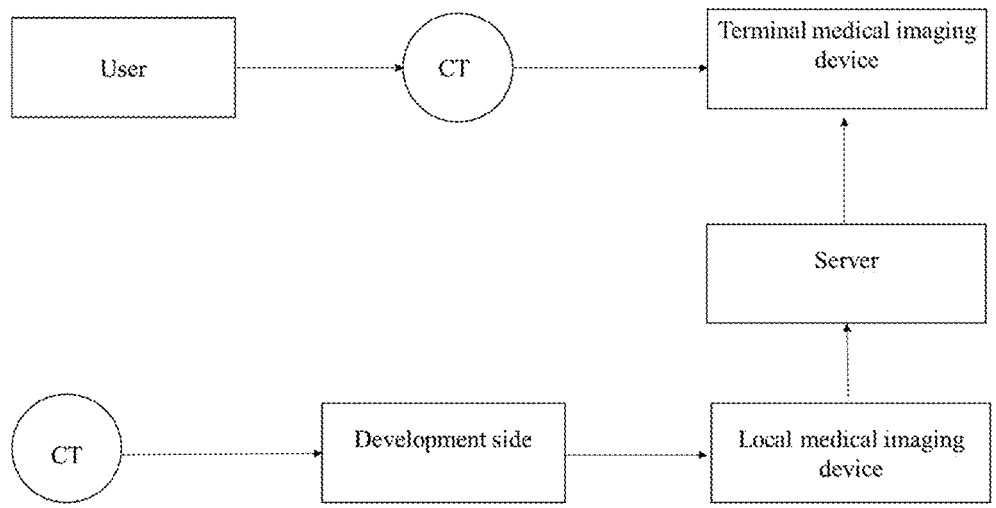
FIG. 3 is a data storage flow chart of the image processing system provided by the invention.

The volume texture data and transfer function results above can be stored in the server 3, and further passed into the volume database 24 of terminal imaging medical device 2 through the server 3. For the data storage process shown in FIG. 3, the users of local medical imaging device 1 or terminal medical imaging device 2 firstly should backup, share and manage the data through local database 13 when using data, and then transfer it to the server 3 through the network for backup, sharing and management, wherein the storage of data is the overall storage. In addition, the ordinary technicians in this field shall be aware that data storage can also be further saved according to the needs of users, so as to facilitate the management of edited three-dimensional human image data and optimize data configuration.

Clients will provide the data of CT disk to the terminal medical imaging device 2, and the volume database 24 will parse the DICOM file in the CT disk to form the volume texture data of client. Then, the volume database 24 will match the volume texture data of client on the basis of stored volume texture data and transfer function results of local medical imaging device, and display the three-dimensional image directly when the matching is successful.

The terminal medical imaging device 2 can access the image source from the server 3 through the network. The image source in server 3 can be from the local medical imaging device 1 or another terminal medical imaging device 2. For example, when two doctors A and B use their own terminal medical imaging device 2 respectively, doctor A can upload the image source to the server 3 for doctor B to obtain, so as to realize the interactive diagnosis between the two doctors. Moreover, if the matching degree is higher than the preset threshold when matching by the volume database 24, the volume texture data parsed of client can be uploaded to the local medical imaging device 1 through the server 3. And reverse rendering editor 11 will edit and adjust the transfer function again until the three-dimensional image for the data of CT disc of the client can be displayed clearly. At the same time, the transfer function results adjusted and the corresponding volume texture data can be transferred to the server 3 for other users to match.

The terminal medical imaging device 2 has a display 21 (such as a computer flat panel display) and a built-in GPU, which is used for dynamic real time rendering of the volume texture data generated by parsing DICOM files. Then they display the three-dimensional human body images after dynamic real time rendering, and present real-time viewing effects with multiple angles, local scaling, lens cutting and stretching of internal organs. When the user views the image through the terminal medical imaging device 2, he/she can not only see the three-dimensional human body image after dynamic real time rendering, but also see the texture 2D/three-dimensional image generated by parsing the original DICOM file corresponding to the three-dimensional human body image.

The local medical imaging device 1 and/or the terminal medical imaging device 2 have HMDS 12 and 22, respectively. The developer or user can view and render three-dimensional human body images and spatial images in real time under the operation state, so as to present the view effect with multiple angles, local zooming, lens clipping and stretching of internal organs in real time. Both HMDS 12 and 22 can offer more realistic three-dimensional virtual reality images. To prevent the viewer from feeling dizzy, the HMDS 22 is set to a minimum FPS (Frames Per Second) of 30 FPS and a maximum FPS of 60 FPS, and the HMDS can be added when the minimum FPS is 30 FPS. The terminal medical imaging device 2 allows the user to select display 21 and/or HMDS 22 for specific image display in the process of specific image display. In addition, the display in local medical imaging device 1 and HMDS 12, and the display 21 and HMDS 22 in terminal medical imaging device 2 can realize the display of the three-dimensional human body image magnified to 60 times. At the same time, the display mode of closing the light is taken as the display mode according to the user's choice.

The operation action refers to the operation and control of the user through an external input 23, such as mouse, keyboard and the like of terminal medical imaging device 2, so as to realize the human-computer interaction. The operation action includes but not limited to: 1) changing the color and/or transparency of a specific organ/tissue, that is the user can adjust the color and/or transparency of individual organs, so as to realize clear distinguishing boundary between the organ and the lesion and high differentiation degree; 2) positioning and scaling the view; 3) rotating the view for multi-angle and 360-degree observation of three-dimensional human body image; 4) "entering" the internal structure of human organs to observe the internal structure, and realizing real-time shear effect rendering; and 5) moving the view up and down.

In addition, the image group for volume data rendering shall be the more, the better. Thus, there are more details as the quantity of figure source data of CD data and the image data group of rendering will affect the final rendering effect. Therefore, the terminal medical imaging device 2 will automatically pick the figure source with the largest data to parse for further rendering. Furthermore, the terminal medical imaging device 2 will select the figure source with thin slice thickness preferentially while picking the figure source automatically, and the scope of slice thickness is 0.2-0.7 mm. In addition, the terminal medical imaging device 2 will obtain the transfer function results formed and edited by the local medical imaging device 1 through the server 3, so as to form the dynamic real time rendering.

Figure 4:
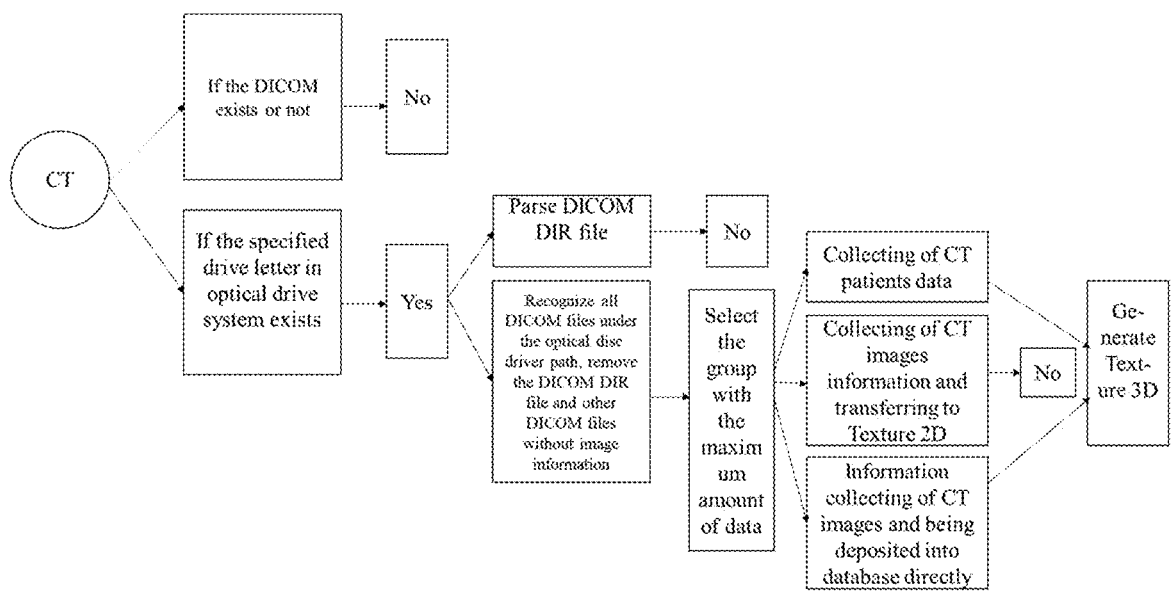
FIG. 4 is a flow chart of resource acquisition of the image processing system provided by the invention.
Figure 5:
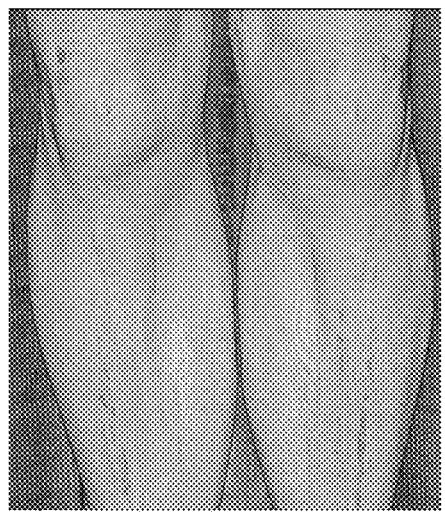
FIG. 5-9 is a display rendering of the display of the terminal medical imaging device of the image processing system provided by the invention.
Figure 6:
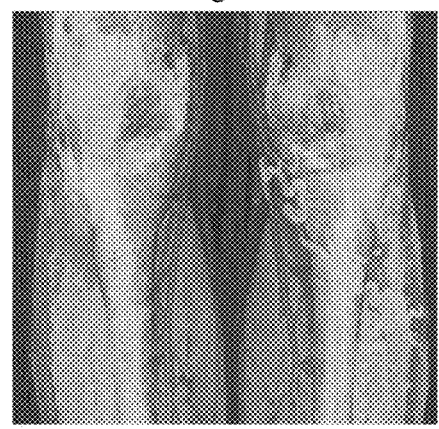
Figure 7:
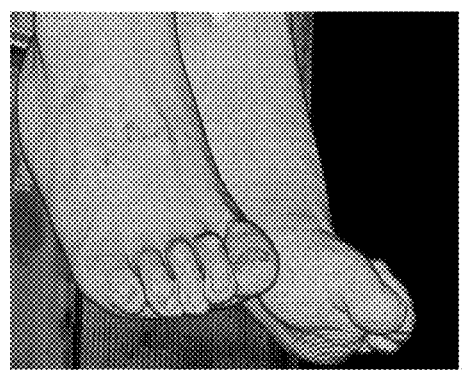
Figure 8:
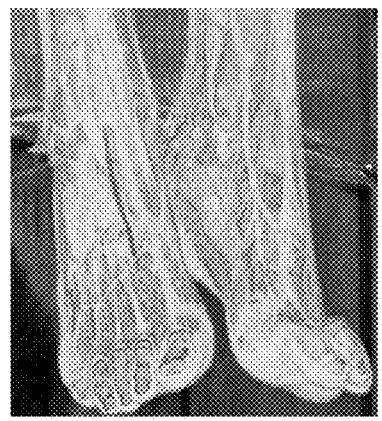
Figure 9:
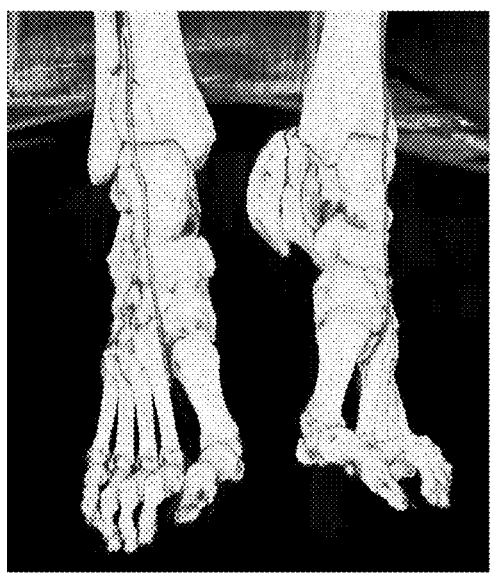
Figure 10:
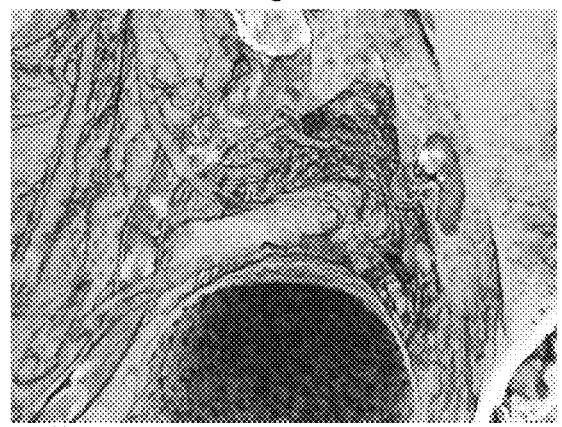
FIG. 10-13 is a rendering of HMDS display of the image processing system provided by the invention.
Figure 11:
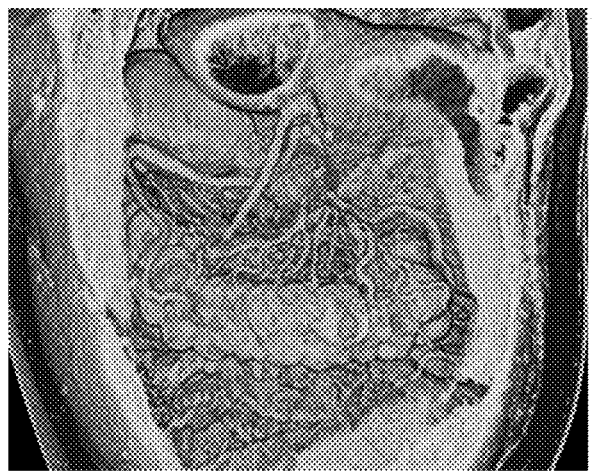
Figure 12:
Figure 13:
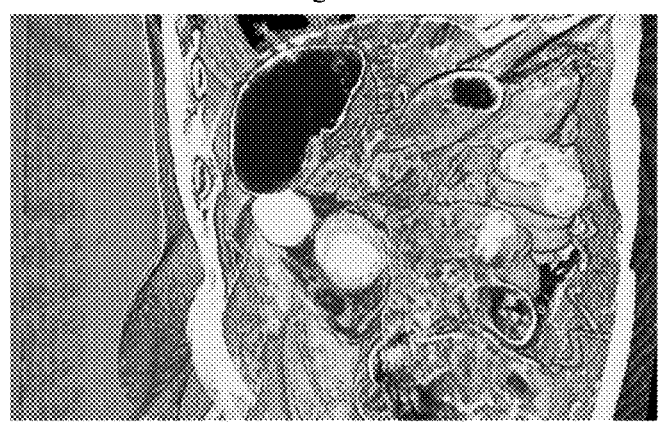
Figure 14:
FIG. 14-17 is a rendering of special display of HMDS of the image processing system provided by the invention.
Figure 15:
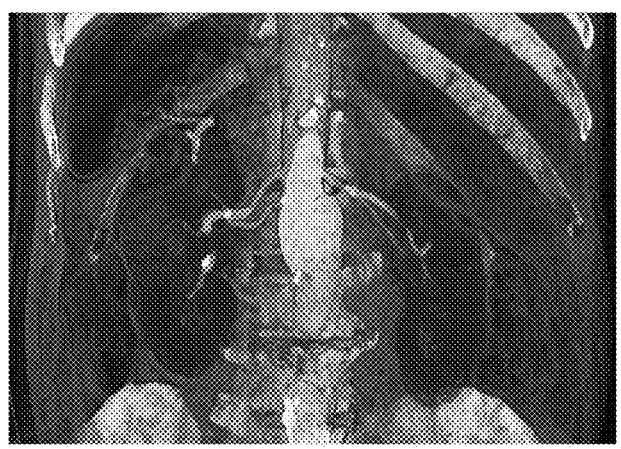
Figure 16:
Figure 17:
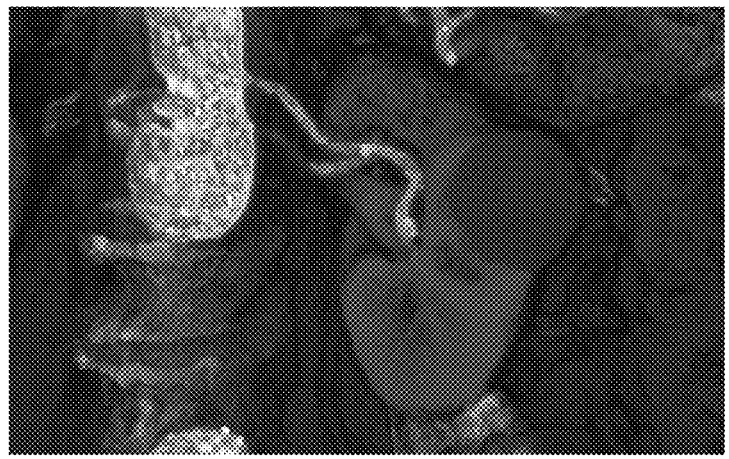

FIG. 4 is a resource acquisition flow chart of the image processing system provided by this invention. The local medical imaging device or terminal medical imaging device will read the DICOM file in the CT disk through the optical drive, and determine whether the CT disk has been read according to the disk symbol of the CT disk and whether the DICOM file has been parsed. When the CT disk has been read and the DICOM file has been parsed, the CT disk will not be subject to resource acquisition. When the CT disk has not been read, the DICOM DIR established will be ignored further to read DICOM files without image information format.

Figure 18:
FIG. 18 is a rendering of tricuspid valve lesions after the original DICOM file was damaged in the existing technology.
Figure 19:
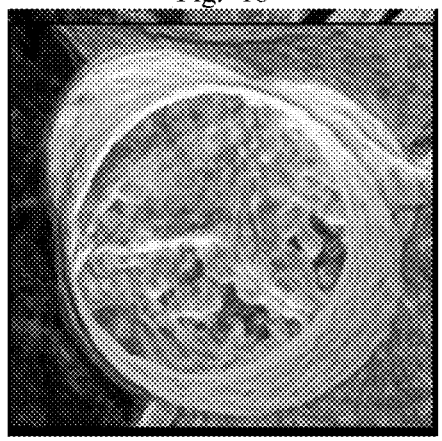
FIG. 19 is a rendering of the lesion in the same position as FIG. 18 displayed by the image processing system provided by the invention.

In a better embodiment, it is different from the existing technology, which is often used, i.e. "eliminating the noise in the image data operation and improving the quality of the image through the filter", the local medical imaging device 1 and/or the terminal medical imaging device 2 all will not destroy the original DICOM file and will not implement filter processing of image in the process of volume rending, so that the edge of the lesion is clear and easy to identify, and the lesion can be identified easily. FIG. 18 shows the imaging effect after filtering and preprocessing of the original DICOM data in the existing technology. In this figure the details of lesions displayed after data damage are reduced greatly, which is not conducive to the diagnosis by doctors. FIG. 19 shows the three-dimensional rendering of the image processing system of the invention on the same part as FIG.

18. It can be seen that the image processing system of the invention presents more detailed details of the lesion and the lesion edge is very clear.

In another better embodiment, the medical imaging system is featured with the rule of special number for the special person, which means that the security and independence among the user data can be realized when the user uses the local medical imaging device 1 to adjust the data deeply for the imaging effect of human internal organs and logs in the local medical imaging device 1 through his/her special account.

The medical imaging system provided by the invention adopts special editing effect of transfer function for volume rendering. For example, the different organs have different colors to form a real organ image, and the organs and lesion bodies to be observed adopt the original color, and other organs adopt blue as the tissue color. The three-dimensional human body image includes the internal organs of the human body and the tissue structure of the same. In addition, different users can edit the same figure source stored on the server separately.

The medical imaging system based on HMDS provided by the invention studies special transfer function algorithm on the basis of using the DICOM file, so that the organ edge is clear and reasonable, the boundaries of the lesion are clear, and the differentiation degree is high. Moreover, the different contrast of color and transparency enhances the three dimensional layering feel, which is a result of big data research algorithm. In the system, the edge line will be shown in the form of points, rather than surface shape. Therefore, the image displayed through the system can reach the high clear visibility to identify lesions.

Furthermore, the local medical imaging device or the terminal medical imaging device will automatically pick a set of DICOM data with the largest data to read, which means it will not read all DICOM arrays. In this way, the device obtains patient information (such as name, gender, collection organs) and CT image information in the CT film, wherein the CT image information will be stored through the local database and subsequently stored to the server. In this step, if the corresponding texture 2D of the CT image has been generated, the CT image information will not be stored.

FIG. 5-9 is an effect image which is displayed by terminal medical imaging device display with image processing system provided by the present invention.

FIG. 10-13 is a rendering of HMDS display of the image processing system provided by the invention, and FIG. 14-17 is a rendering of special display of HMDS of the image processing system provided by the invention, wherein the special display refers to the special contrast processing of interested organs or tissues, which is realized by changing the color and/or transparency of the organs or tissues through the reverse rendering editor.

This point is well shown in Embodiment 3: secondary three-dimensional reconstruction.

In the three-dimensional image which has been formed, the image processing system of the invention can be viewed and adjusted in allusion to the selected area. And the detailed internal images of a specific part or lesion of an organ can be checked separately while preventing the effect to the other parts unselected. In addition, the lesion can be judged according to the color transparency in the case of multiple sites, so that the influence of the surrounding parts or other organs can be eliminated.

That is to say, the image processing system of the invention realizes the secondary three-dimensional reconstruction in any area of volume data, and user can select an area (for example, selection by clicking, circling and boxing) of the three-dimensional image formed to enhance the three-dimensional effect of this area. The secondary three-dimensional reconstruction can magnify the rendering without distortion.

Specifically, the image processing system of the invention can capture the volume data of the secondary reconstruction area from the first three-dimensional image according to the user's instruction, match the transfer function result such as positioning display depth, support the amplification and accurate position of selected area, see the internal structure clearly, and realize precision medicine.

Figure 20A:
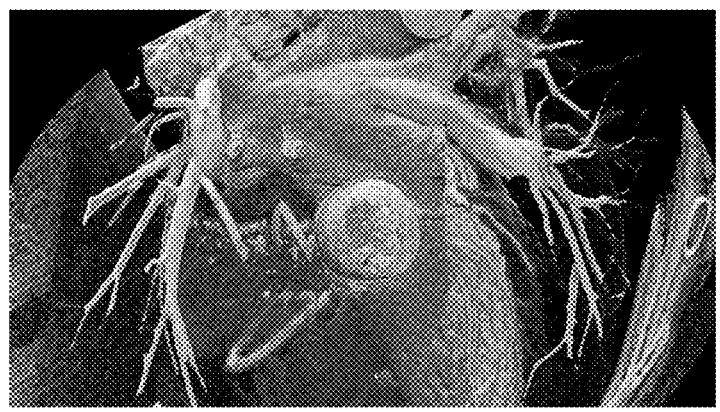
FIG. 20(*a*) is the second three-dimensional reconstruction rendering of the selection area of tricuspid valve lesion by the image processing system provided by the invention.
Figure 20B:
Figure 20C:
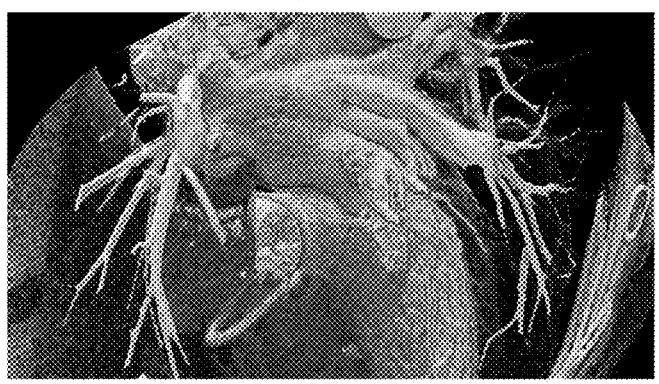

FIG. 20(a)-20(c) shows a rendering of secondary three-dimensional reconstruction of tricuspid valve lesions.

Figure 21A:
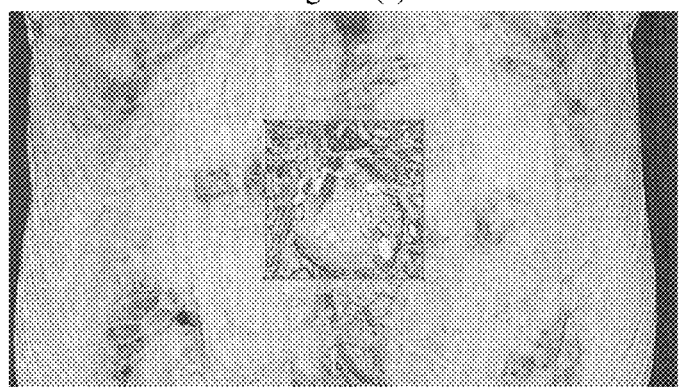
FIG. 21(*a*) is a rendering of the second three-dimensional reconstruction of the image processing system provided by the invention to the selection area of aortic aneurysm.
Figure 21B:
Figure 21C:
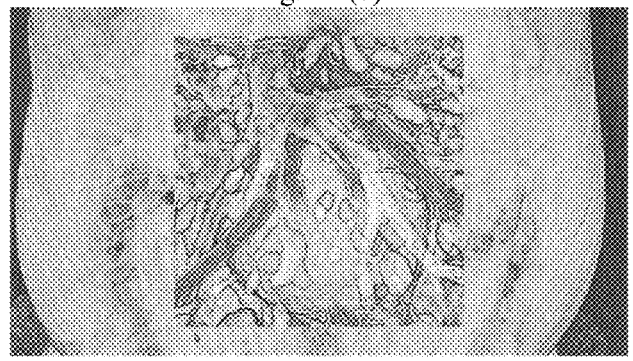

FIG. 21(a)-21(c) shows a rendering of secondary three-dimensional reconstruction of aortic aneurysm lesions.

Figure 22A:
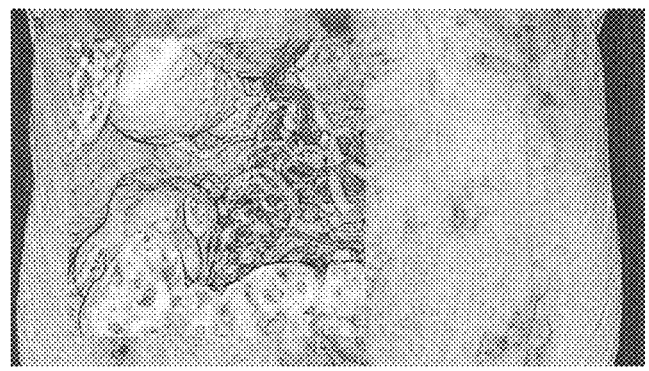
FIG. 22(*a*) is a rendering of the second three-dimensional reconstruction of the image processing system provided by the invention to the selection area of kidney tumor.
Figure 22B:
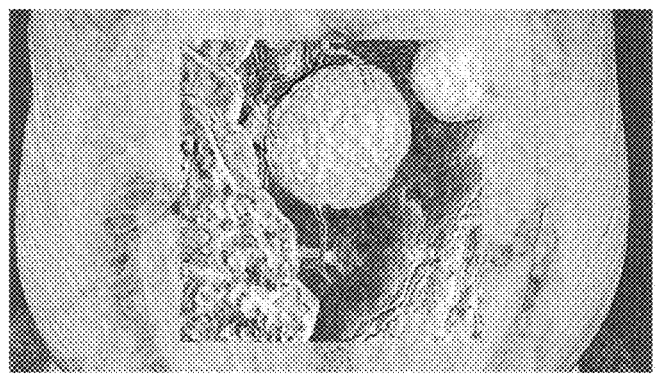

FIG. 22(a)-22(b) shows a rendering of secondary three-dimensional reconstruction of renal tumor lesions.

Figure 23A:
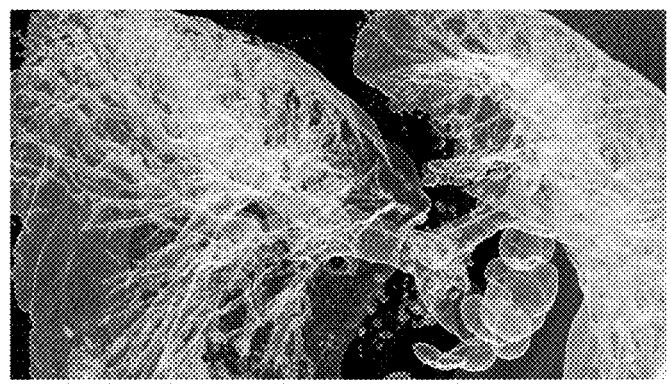
FIG. 23(*a*) is a three-dimensional image of the image processing system provided by the invention to the inner wall of the lung and bronchus.
Figure 23B:
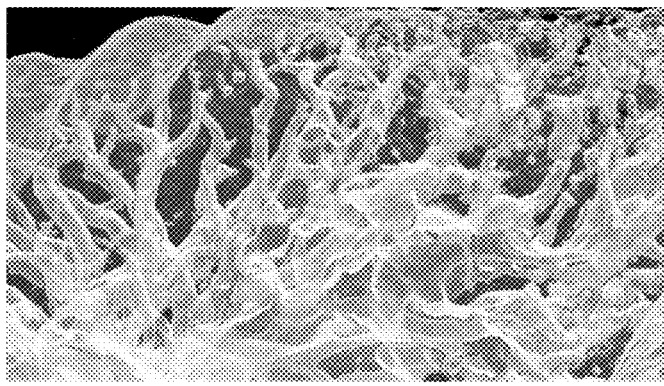

FIG. 23(a)-23(b) shows an enlarged three-dimensional rendering of the inner wall of the lung and bronchus.

Figure 24:
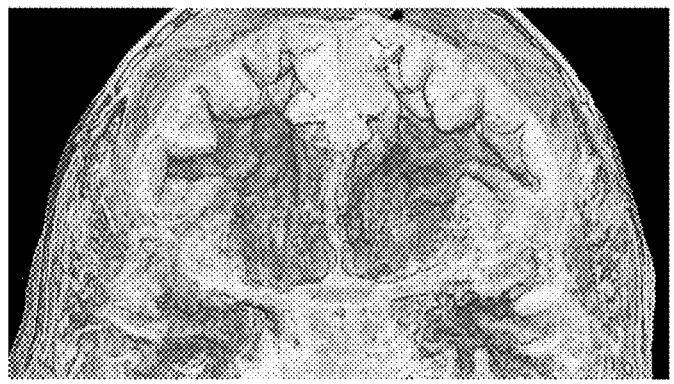
FIG. 24 is a three-dimensional MRI brain image of the image processing system provided by the invention.

FIG. 24 is a three-dimensional MRI brain image of the image processing system provided by the invention.

Figure 25A:
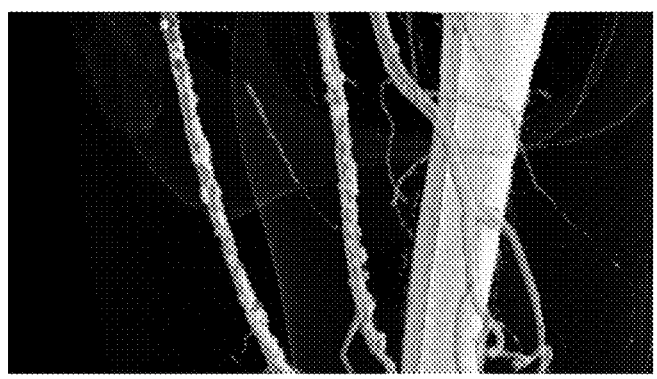
FIG. 25(*a*) is a three-dimensional image A of the image processing system provided by the invention to main vascular lesion.
Figure 25B:
Figure 25C:

FIG. 25(a)-25(c) shows a three-dimensional image rendering of the main vascular lesion.

Compared with prior art, the image processing system and method provided by the invention have the following advantages: I. The human body imaging effect is more real, steric and intuitive, and doctors can identify patient organs and identify lesions automatically; II. It realizes the interactive display of three-dimensional human body imaging, thus doctors can do positioning zoom, rotation view for multi-angle view, "entering" the internal structure of human organs to observe the internal structure by stretching the view, moving the view from top to bottom, changing color and transparency in a particular area to highlight a particular organ or tissue structure; III. The medical imaging based on HMDS (head-mounted displays set) is clearer, the dead corners that cannot be seen in two dimensional view can be seen, interaction and immersion are enhanced; IV. The server and the local database store data together, and they share and manage and optimize resource allocation; V. The security and independence among the user data are ensured through the setting of special personnel and special account.

Unless otherwise specified, the qualifiers such as "the first" and "the second" in this paper do not refer to the qualification of time sequence, quantity or importance, but merely to distinguish one technical feature from another in this technical scheme. Similarly, the qualifiers such as "one" in this paper do not refer to the quantitative qualification, but describe the technical characteristics that did not appear in the previous paper. Similarly, the modifiers such as "about" and "approximately" that appear before the numerals in this paper usually contain the number, and their specific meanings shall be understood in the context. Similarly, unless the noun is modified by a specific quantitative quantifier, it shall be regarded in this paper as including both singular and plural forms. In this technical scheme, both singular and plural technical features can be included.

The embodiments described in this specification are only better concrete ones of the invention. The embodiments above are only used to describe the technical scheme of the invention and are not limitations of the invention. Technical scheme that can be obtained by logical analysis, reasoning or limited experiments according to the conception of the invention by technicians in the field shall be within the scope of the invention.

What is claimed is:

1. An image processing system, including:
a local medical imaging device, comprising a local database and a reverse rendering editor, wherein the local database comprises a parsing module and a storage module, the parsing module is used to parse a first DICOM file to form a first volume texture data and save in the storage module wherein the reverse rendering editor is used for receiving the first volume texture data and generating a corresponding transfer function result through a transfer function model;
a server connected with the local medical imaging device for storing the first volume texture data and the corresponding transfer function results;
a terminal medical imaging device, including a user input interface and a volume database, wherein the volume database is connected with the server and used to obtaining the first volume texture data and the corresponding transfer function results, wherein the volume database is used to parse a second DICOM file input from the user input interface to form a second volume texture data, then the volume database find the first volume texture data and the transfer function results with the matching degree within a preset threshold, and show a first three-dimensional image;
when the matching degree is higher than the preset threshold, the terminal medical imaging device will transfer the second volume texture data to the local medical imaging device through the volume database, and the reverse rendering editor edit and adjust the transfer function model and transfer function results, then the reverse rendering editor transmit the adjusted transfer function results to the terminal medical imaging device through the server and show a second three-dimensional image; and one or more displays configured on the local medical imaging device and/or the terminal medical imaging device respectively.

2. The image processing system according to claim 1, wherein the first DICOM file is the same as the second DICOM file.

3. The image processing system according to claim 1, wherein both the local medical imaging device and the terminal imaging medical device are equipped with a head-mounted display.

4. The image processing system according to claim 3, wherein the head-mounted display is a VR device.

5. An image processing method performed by the image processing system of claim 1, including the following steps:
(i) Obtaining the first volume texture data and the corresponding transfer function results from the server, and saving them in the volume database;
(ii) Providing the second DICOM file to the terminal medical imaging device;
(iii) Searching the first texture data and the corresponding transfer function results within the preset threshold matching to the second DICOM file in the volume database, and displaying the second three-dimensional image.

6. The image processing method according to claim 5, wherein the step (iii) also includes a step of parsing the second DICOM file to form the second volume texture data in the volume database.

7. The image processing method according to claim 5, wherein the second three-dimensional image is displayed via a head-mounted display, preferably a VR device.

8. The image processing method according to claim 5, wherein the second three-dimensional image is the same as the first three-dimensional image.

9. The image processing method according to claim 5, wherein the matching in step (iii) is selected from the following groups: organ parameters, frame, row, column, resolution, and/or slice thickness.

10. The image processing method according to claim 5, wherein the second volume texture data will be transferred to the local medical imaging device through the server when the matching degree is higher than the preset threshold specified in step (iii), then the reverse rendering editor will edit and adjust the transfer function and transfer the transfer function results adjusted to the terminal medical imaging device through the server to display the second three-dimensional image.

11. An image processing method performed by the image processing system of claim 1, including the following steps:
(1) Obtaining the first texture data and the corresponding transfer function results from the server, and saving them in the database;
(2) Providing the second DICOM file to the terminal medical imaging device;
(3) Searching the first texture data and the corresponding transfer function results within the preset threshold matching to the second DICOM file in the volume database, and displaying the second three-dimensional image;
(4) Providing a region selection command to form a selection region in the second three-dimensional image, then searching the transfer function result with the preset threshold matching degree with the selection region in the volume database, and displaying a third three-dimensional image of the selection region.

12. The image processing method according to claim 11, wherein the data of the selection region will be transferred to the local medical imaging device through the server when the matching degree is higher than the preset threshold specified in step (4), and then the reverse rendering editor will edit and adjust the transfer function and transfer the transfer function results adjusted to the terminal medical imaging device through the server to display the third three-dimensional image.

* * * * *